(12) United States Patent
Berberich

(10) Patent No.: US 9,427,246 B2
(45) Date of Patent: Aug. 30, 2016

(54) MEDICAL CUTTING INSTRUMENT FOR CUTTING MUSCLES AND TENDONS

(75) Inventor: Sascha Berberich, Tuttlingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 179 days.

(21) Appl. No.: 13/547,854

(22) Filed: Jul. 12, 2012

(65) Prior Publication Data

US 2013/0018404 A1    Jan. 17, 2013

(30) Foreign Application Priority Data

Jul. 13, 2011    (DE) .................... 10 2011 107 178

(51) Int. Cl.
| | |
|---|---|
| A61B 17/295 | (2006.01) |
| A61B 17/32 | (2006.01) |
| A61B 17/00 | (2006.01) |

(52) U.S. Cl.
CPC . *A61B 17/320016* (2013.01); *A61B 17/00008* (2013.01); *A61B 17/295* (2013.01); *A61B 2017/00353* (2013.01); *A61B 2017/320064* (2013.01)

(58) Field of Classification Search
CPC .................... A61B 17/295; A61B 17/320016; A61B 2017/320064; A61B 2017/00653; A61B 17/3205; A61B 2017/00969
USPC ............ 606/167–180, 184–186, 205–208, 1, 606/120
See application file for complete search history.

(56) References Cited

U.S. PATENT DOCUMENTS

| | | | |
|---|---|---|---|
| 253,359 A | 2/1882 | Ewing | |
| 865,551 A * | 9/1907 | Wells | 606/174 |
| 1,079,128 A * | 11/1913 | Howe | A61B 17/3201 30/229 |
| 2,706,987 A * | 4/1955 | Bramstedt | 606/147 |
| 3,006,344 A * | 10/1961 | Vogelfanger | 606/143 |
| 3,391,690 A * | 7/1968 | Armao | A61B 17/2812 30/140 |
| 3,404,677 A * | 10/1968 | Springer | A61B 17/29 30/135 |
| 3,631,858 A * | 1/1972 | Ersek | 606/120 |
| 3,763,860 A | 10/1973 | Clarke | |
| 4,243,047 A * | 1/1981 | Olsen | 600/564 |

(Continued)

FOREIGN PATENT DOCUMENTS

| | | |
|---|---|---|
| DE | 10003020 A1 | 8/2001 |
| WO | 03011152 A1 | 2/2003 |

OTHER PUBLICATIONS

German Search Report; Application No. DE 10 2011 107 178.8; Issued: Apr. 20, 2012; 5 pages.

*Primary Examiner* — Ruan J Severson
*Assistant Examiner* — Christian Knauss
(74) *Attorney, Agent, or Firm* — Whitmyer IP Group LLC

(57) ABSTRACT

A medical cutting instrument for cutting muscles and tendons, having a shaft on whose distal end a tool is mounted consisting of two jaw members, such that at least one jaw member can move with respect to the other jaw member, and on whose proximal end a handle is mounted, such that the movable jaw member and the handle operatively interact with one another by way of an actuation element mounted in the shaft in such a way that the movable jaw member can be shifted between a closed position and an opened position of the tool by actuating the handle and whereby the tool is configured for simultaneous severing and holding of one end of the severed muscle/tendon tissue. At least in the other jaw member, a guide is configured for controlled insertion of the muscle/tendon tissue that is to be severed.

15 Claims, 6 Drawing Sheets

(56) References Cited

U.S. PATENT DOCUMENTS

| | | | | |
|---|---|---|---|---|
| 4,522,206 | A * | 6/1985 | Whipple et al. | 606/174 |
| 4,590,936 | A * | 5/1986 | Straub et al. | 606/174 |
| 4,597,385 | A * | 7/1986 | Watson | 600/564 |
| 4,600,007 | A * | 7/1986 | Lahodny et al. | 606/174 |
| 4,763,669 | A * | 8/1988 | Jaeger | 600/564 |
| 4,815,460 | A * | 3/1989 | Porat et al. | 606/207 |
| 4,919,152 | A * | 4/1990 | Ger | 128/898 |
| 4,955,897 | A | 9/1990 | Ship | |
| 4,971,067 | A * | 11/1990 | Bolduc et al. | 600/564 |
| 4,994,024 | A * | 2/1991 | Falk | 604/22 |
| 5,071,424 | A | 12/1991 | Reger | |
| 5,174,300 | A * | 12/1992 | Bales et al. | 600/564 |
| 5,196,023 | A * | 3/1993 | Martin | 606/148 |
| 5,217,460 | A * | 6/1993 | Knoepfler | 606/52 |
| 5,219,354 | A * | 6/1993 | Choudhury et al. | 606/174 |
| 5,234,453 | A * | 8/1993 | Smith et al. | 606/170 |
| 5,254,129 | A * | 10/1993 | Alexander | A61B 17/295 30/135 |
| 5,260,415 | A * | 11/1993 | David | 528/495 |
| 5,282,484 | A * | 2/1994 | Reger | 128/898 |
| 5,286,255 | A * | 2/1994 | Weber | 604/22 |
| 5,304,203 | A * | 4/1994 | El-Mallawany et al. | 606/207 |
| 5,368,606 | A * | 11/1994 | Marlow et al. | 606/170 |
| 5,383,471 | A * | 1/1995 | Funnell | 600/564 |
| 5,389,104 | A * | 2/1995 | Hahnen et al. | 606/174 |
| 5,395,375 | A * | 3/1995 | Turkel et al. | 606/83 |
| 5,417,701 | A * | 5/1995 | Holmes | 606/148 |
| 5,431,674 | A * | 7/1995 | Basile et al. | 606/170 |
| 5,439,471 | A * | 8/1995 | Kerr | 606/174 |
| 5,484,447 | A * | 1/1996 | Waldock et al. | 606/107 |
| 5,531,756 | A * | 7/1996 | Larose | 606/184 |
| 5,569,299 | A * | 10/1996 | Dill et al. | 606/205 |
| 5,620,415 | A * | 4/1997 | Lucey | A61B 17/1608 604/22 |
| 5,643,307 | A * | 7/1997 | Turkel et al. | 606/184 |
| 5,683,359 | A * | 11/1997 | Farkas et al. | 604/22 |
| 5,797,922 | A * | 8/1998 | Hessel et al. | 606/120 |
| 5,797,936 | A * | 8/1998 | Kleihues | 606/167 |
| 5,810,883 | A * | 9/1998 | Lang | 606/207 |
| 5,851,214 | A * | 12/1998 | Larsen et al. | 606/170 |
| 5,893,878 | A * | 4/1999 | Pierce | 606/207 |
| 5,906,629 | A * | 5/1999 | Oren et al. | 606/205 |
| 5,984,938 | A | 11/1999 | Yoon | |
| 6,015,412 | A * | 1/2000 | Mifsud | 606/83 |
| 6,024,744 | A * | 2/2000 | Kese et al. | 606/51 |
| 6,030,409 | A * | 2/2000 | Lang | 606/205 |
| 6,077,280 | A | 6/2000 | Fossum | |
| 6,102,925 | A * | 8/2000 | Oren et al. | 606/170 |
| 6,183,484 | B1 * | 2/2001 | Matsutani et al. | 606/144 |
| 6,358,249 | B1 * | 3/2002 | Chen et al. | 606/45 |
| 6,391,043 | B1 * | 5/2002 | Moll et al. | 606/174 |
| 6,419,684 | B1 * | 7/2002 | Heisler et al. | 606/170 |
| 6,974,453 | B2 * | 12/2005 | Woloszko et al. | 606/41 |
| 6,976,992 | B2 * | 12/2005 | Sachatello et al. | 606/205 |
| 7,087,070 | B2 * | 8/2006 | Flipo | 606/205 |
| 7,174,640 | B2 * | 2/2007 | Elkins | 30/357 |
| 7,871,423 | B2 * | 1/2011 | Livneh | 606/205 |
| 7,951,150 | B2 * | 5/2011 | Johnson et al. | 606/51 |
| 2001/0021861 | A1 * | 9/2001 | Boebel et al. | 606/207 |
| 2001/0044635 | A1 * | 11/2001 | Niizeki et al. | 606/205 |
| 2002/0183784 | A1 * | 12/2002 | Lutze et al. | 606/206 |
| 2004/0102800 | A1 * | 5/2004 | Li et al. | 606/167 |
| 2006/0258954 | A1 * | 11/2006 | Timberlake et al. | 600/564 |
| 2007/0244515 | A1 * | 10/2007 | Fanous | 606/205 |
| 2008/0208221 | A1 * | 8/2008 | Murray et al. | 606/145 |
| 2008/0215079 | A1 * | 9/2008 | Collins et al. | 606/167 |
| 2009/0043323 | A1 * | 2/2009 | Alleyne | 606/167 |
| 2009/0062816 | A1 * | 3/2009 | Weber | 606/144 |
| 2009/0131933 | A1 * | 5/2009 | Ghabrial et al. | 606/51 |
| 2010/0016868 | A1 * | 1/2010 | Kim | 606/144 |
| 2011/0224718 | A1 * | 9/2011 | Torgerson | 606/207 |
| 2011/0295297 | A1 * | 12/2011 | Shirley et al. | 606/184 |
| 2013/0018403 | A1 * | 1/2013 | Berberich | 606/174 |

* cited by examiner

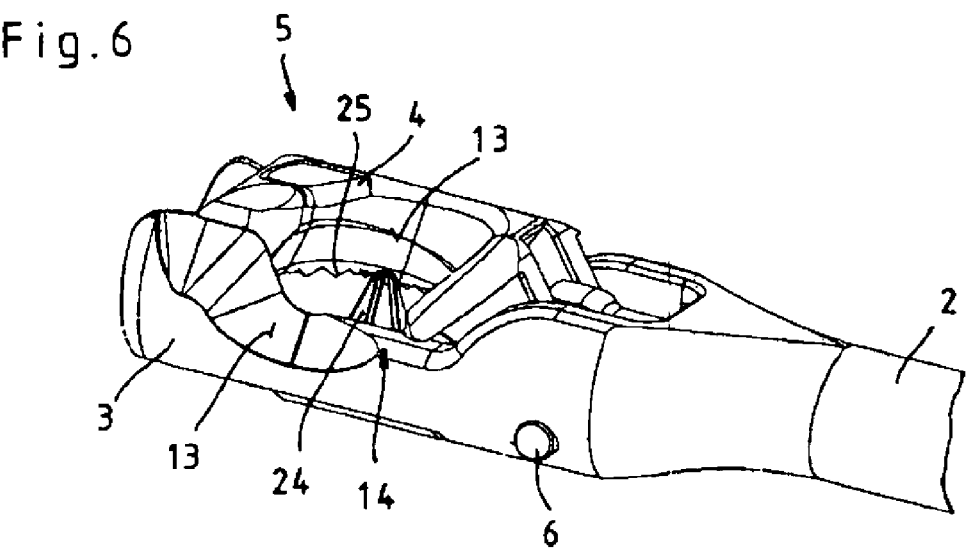
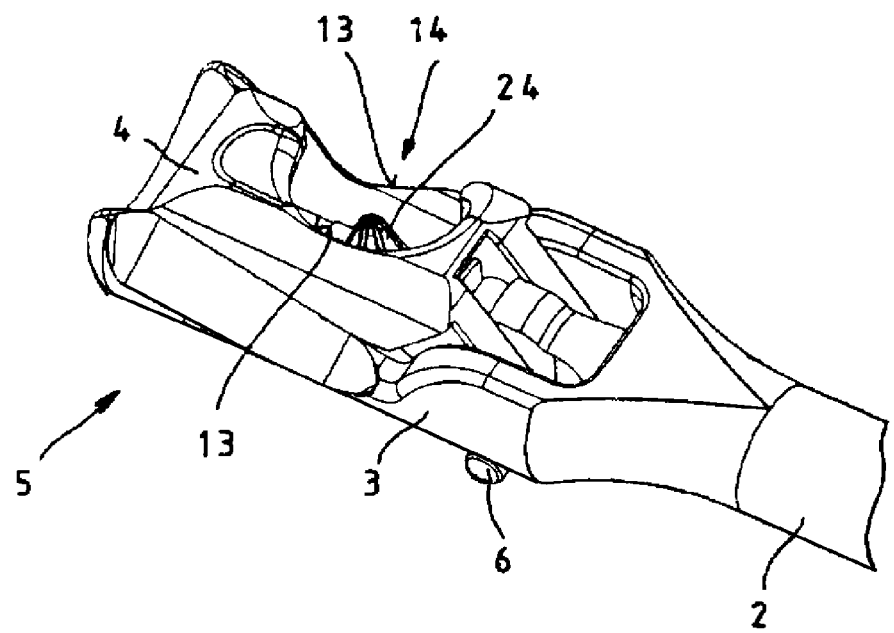

MEDICAL CUTTING INSTRUMENT FOR CUTTING MUSCLES AND TENDONS

CROSS-REFERENCE TO RELATED APPLICATIONS

The present application claims priority of German patent application No. 10 2011 107 178.8 filed on Jul. 13, 2011, the content of which is incorporated herein by reference.

FIELD OF THE INVENTION

The invention relates to a medical cutting instrument for cutting muscles and tendons, having a shaft on whose distal end a tool is mounted consisting of two jaw members, such that at least one jaw member is configured as a jaw member that can move with respect to the other jaw member, and on whose proximal end a handle is mounted, such that the movable jaw member and the handle operatively interact with one another by way of an actuating element mounted in the shaft, in such a way that the movable jaw member can be shifted by actuating the handle between a closed position and an opened position of the tool and such that the tool is configured for simultaneous severing and holding one end of the severed muscle/tendon tissue.

BACKGROUND OF THE INVENTION

Generic medical cutting instruments are used, for example, in biceps tenotomy or biceps tenodesis operations in order to sever the biceps tendon if said tendon causes pains in the joint from wear and tear.

From DE 100 03 020 A1, a bipolar medical gripping instrument is known whose tool is configured for simultaneous severing and holding of one end of the severed muscle/tendon tissue. With this known medical instrument for holding and cutting of vessels, the cutting device is mounted in the center of the clamping surfaces of the jaw members. The arrangement of the cutting device as well as of the clamping surfaces of the jaw members does not allow, however, the controlled severing of muscle and tendon tissue.

An additional medical cutting instrument for cutting muscles and tendons is known, for example, from U.S. Pat. No. 253,359. With this known instrument it is possible to make an incision that exposes a tendon, to savage said tendon and to sever a piece from the tendon tissue.

Contrary to open surgery, in which the tendon is severed blindly because it is desired not to open up the site, the tendon in arthroscopy is visible, but first, before severing, must be secured by attaching and arthroscopic suturing in order to prevent the tendon from withdrawing immediately back to the base and then requiring salvaging by means of open surgery.

SUMMARY OF THE INVENTION

It is consequently the object of the invention to provide a medical cutting instrument of the aforementioned type, which is both simple to operate and allows controlled severing of the muscle/tendon tissue.

This object is achieved, according to the invention, in a manner characterized by the features of claim 1. Here, at least in the other jaw member, a guide is configured for guided reception of the muscle/tendon tissue that is to be severed.

Advantageous refinements of the invention are the subject of the dependent claims.

Owing to the configuration of the tool as combined cutting and holding tool, it is possible to keep a firm grasp on one end of the muscle or tendon tissue, which was severed in the first working step with the same instrument, and thus to prevent its retracting.

To ensure that the muscle/tendon tissue that is to be severed is aligned correctly with the cutting edge and with the clamping surfaces, guides for controlling the insertion of the muscle/tendon tissue that is to be severed are configured at least in the other jaw member, preferably in both jaw members.

According to a practical embodiment of the invention, it is proposed that to hold the severed muscle/tendon tissue, mutually corresponding clamping surfaces should be mounted on both jaw members, such that the clamping surfaces are preferably configured as toothed connections that engage with one another and are aligned diagonally to the instrument longitudinal axis.

It is proposed with an alternative embodiment of the invention that the clamping surfaces should be configured as individual teeth separated from one another by diagonal and lengthwise indentations. The configuration as individual teeth ensures a secure grip and good lateral safety from sliding for the severed muscle or tendon tissue.

It is further proposed with the invention that the toothed connection or the individual teeth configured on the clamping surfaces and oriented diagonally should be inclined toward the distal side, at least in part, in order to ensure better wedging and fastening of the severed muscle or tendon tissue, because thanks to the distal inclination, the tissue, which tries to retract toward the proximal end, is pressed more firmly against the toothed connection or the individual teeth. This effect is intensified with an increase in the number of inclined toothed connections or individual teeth of the clamping surfaces.

It is further proposed with the invention to configure the clamping surfaces as a solitary individual tooth mounted on the rigid jaw member and as a row of teeth running along the indentation.

To configure the cutting function, it is proposed according to the invention that at least on the movable jaw member a cutting edge should be configured that, according to a preferred embodiment of the invention, is oriented downward toward the other jaw member on the distal end of the movable jaw member.

It is proposed with an alternative embodiment of the invention that the cutting edge should be oriented downward toward the other jaw member and configured as U-shaped, and disposed on the movable jaw member in such a way that the cutting edge extends from the distal end of the movable jaw member to both lateral areas of the movable jaw member. This configuration of the cutting edge has the advantage that a secure cutting result can be achieved precisely in difficult cutting situations, for example cutting through unusually thick tendons or through the tendon sheath.

To ensure precise and complete severing of the muscle or tendon tissue upon closing the movable jaw member, it is proposed with the invention that in the area of the cutting edge mounted on the movable jaw member, a recess should be configured in the other jaw member to insert the cutting edge, said recess being configured as an indentation or a pass-through opening in the rigid jaw member.

It is further proposed with the invention that the clamping surface should be mounted on the movable jaw member proximally behind the cutting edge and/or the clamping surface should be positioned on the other jaw member proximally behind the recess for receiving the cutting edge in order to be able to fasten one end of the severed tissue by clamping directly after the severing.

It is finally proposed with the invention that the distal end of the other jaw member, which extends beyond the movable jaw member in the axial direction, should be of rounded configuration in order to facilitate penetration of the medical cutting instrument through soft parts by means of dilator-shaped configuration of the distal instrument tip.

To adjust and shift the cutting depth, it is proposed with the invention that in the area of the handle a lever mechanism should be provided that configures a variable stop for closing the two jaw members with respect to one another and thus causes the shifting of the cutting depth.

It is further proposed with the invention that a scale should be mounted on the handle in order to be able to sever the muscle/tendon tissue by choice at a determined depth.

Further features and advantages of the invention can be seen from the related drawings, in which four embodiments of an inventive medical cutting instrument for cutting muscles and tendons are illustrated only by way of example, without restricting the invention to these embodiments.

BRIEF DESCRIPTION OF THE DRAWINGS

FIG. 6 shows a perspective front view of a tool according to a fourth inventive embodiment.

FIG. 7 shows a perspective rear view of the tool according to FIG. 6.

DETAILED DESCRIPTION OF THE INVENTION

Figure 1:
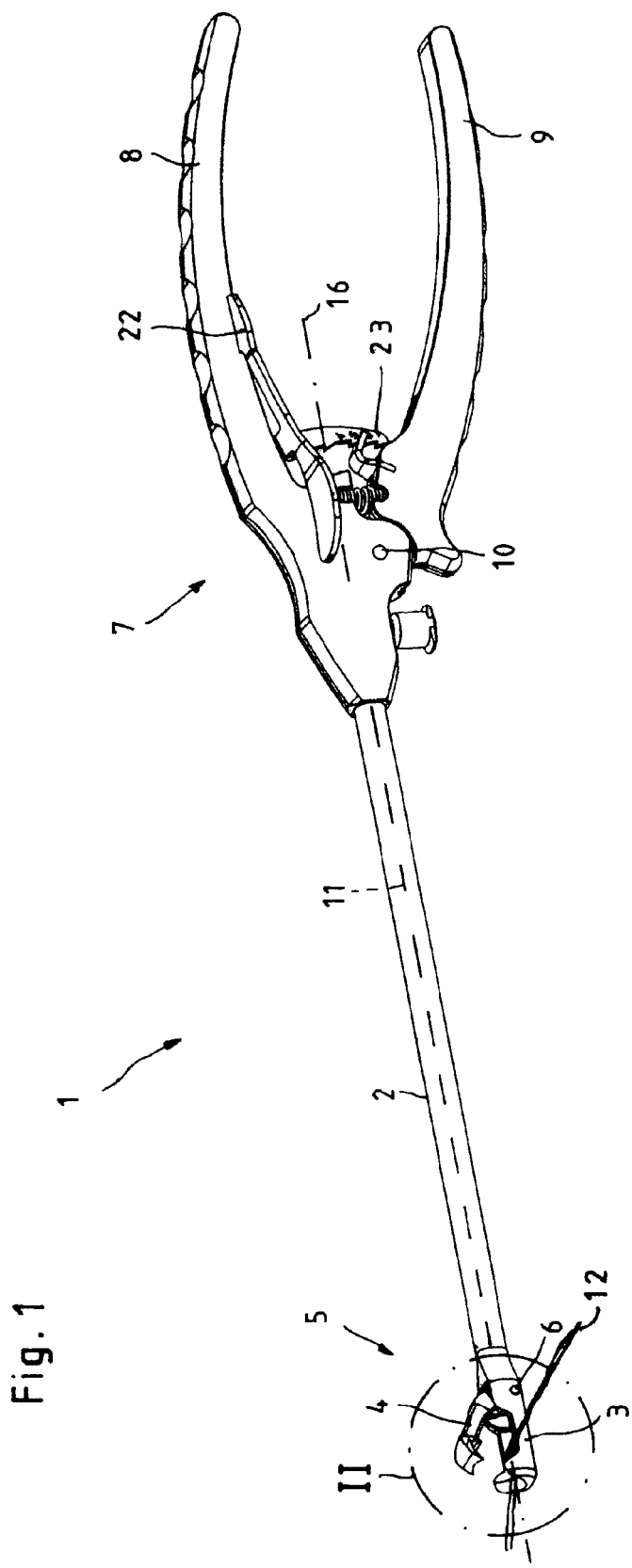
FIG. 1 shows a schematic side view of a first embodiment of an inventive medical cutting instrument for cutting muscles and tendons.

FIG. 1 shows a perspective view of a medical cutting instrument 1 for cutting muscles and tendons.

This cutting instrument 1, configured for example as a biceps tendon punch and usable both in open surgery and in arthroscopic surgery, comprises a shaft 2 on whose distal end is mounted a tool 5 consisting of two jaw members 3 and 4, such that one jaw member 3 is of rigid configuration and the other jaw member 4 is configured as a jaw member 4 that can be pivoted with respect to the rigid jaw member 3 about a pivot axis 6. Mounted on the proximal end of the shaft 2 is a handle 7, which in the illustrated embodiment consists of two gripping members 8 and 9, such that one gripping member 8 is of rigid configuration and the other gripping member 9 is configured as a gripping member 9 that can be pivoted with respect to the rigid gripping member 8 about a pivot axis 10.

Figure 2:
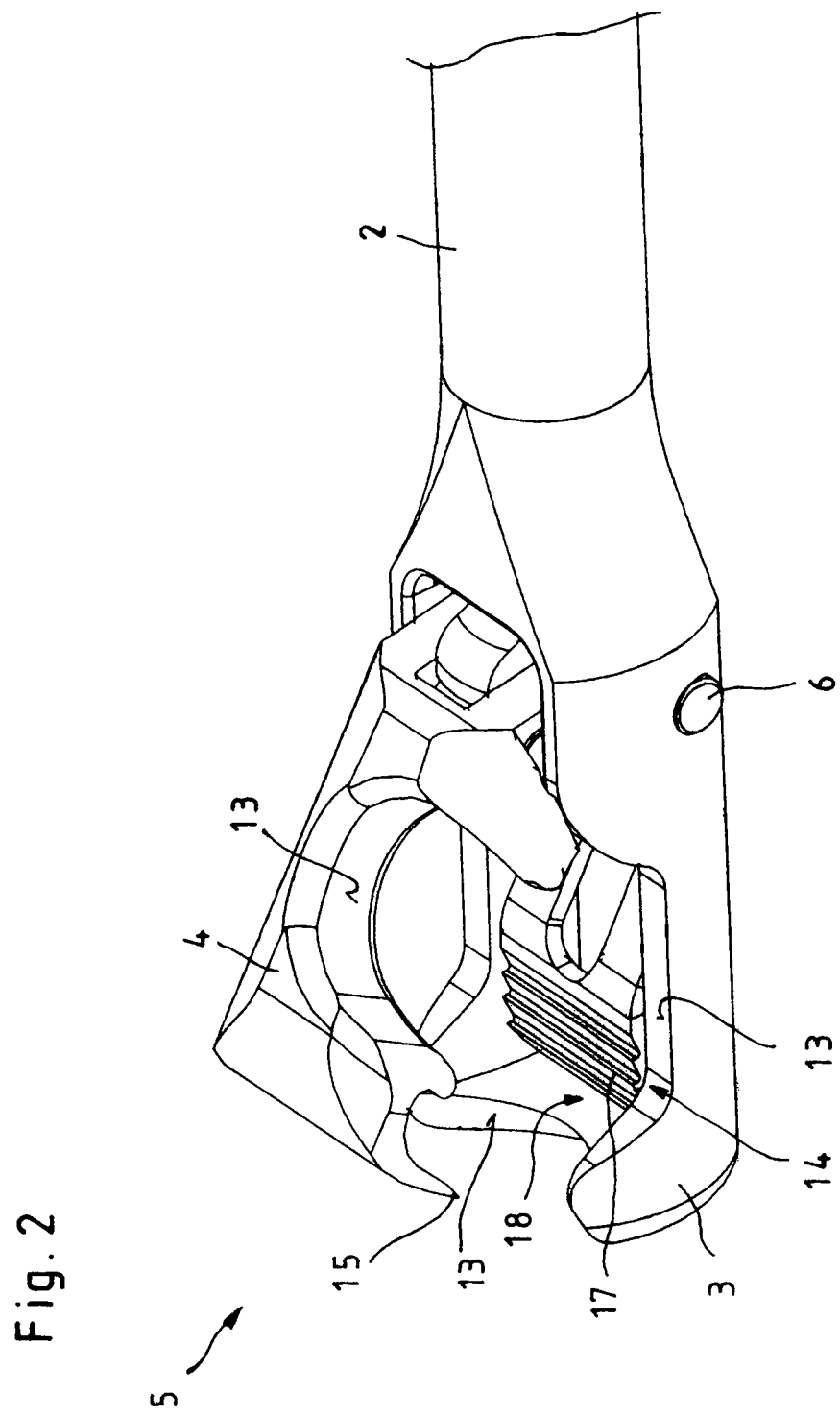
FIG. 2 shows an enlarged perspective overhead view of detail II from FIG. 2.
Figure 3:
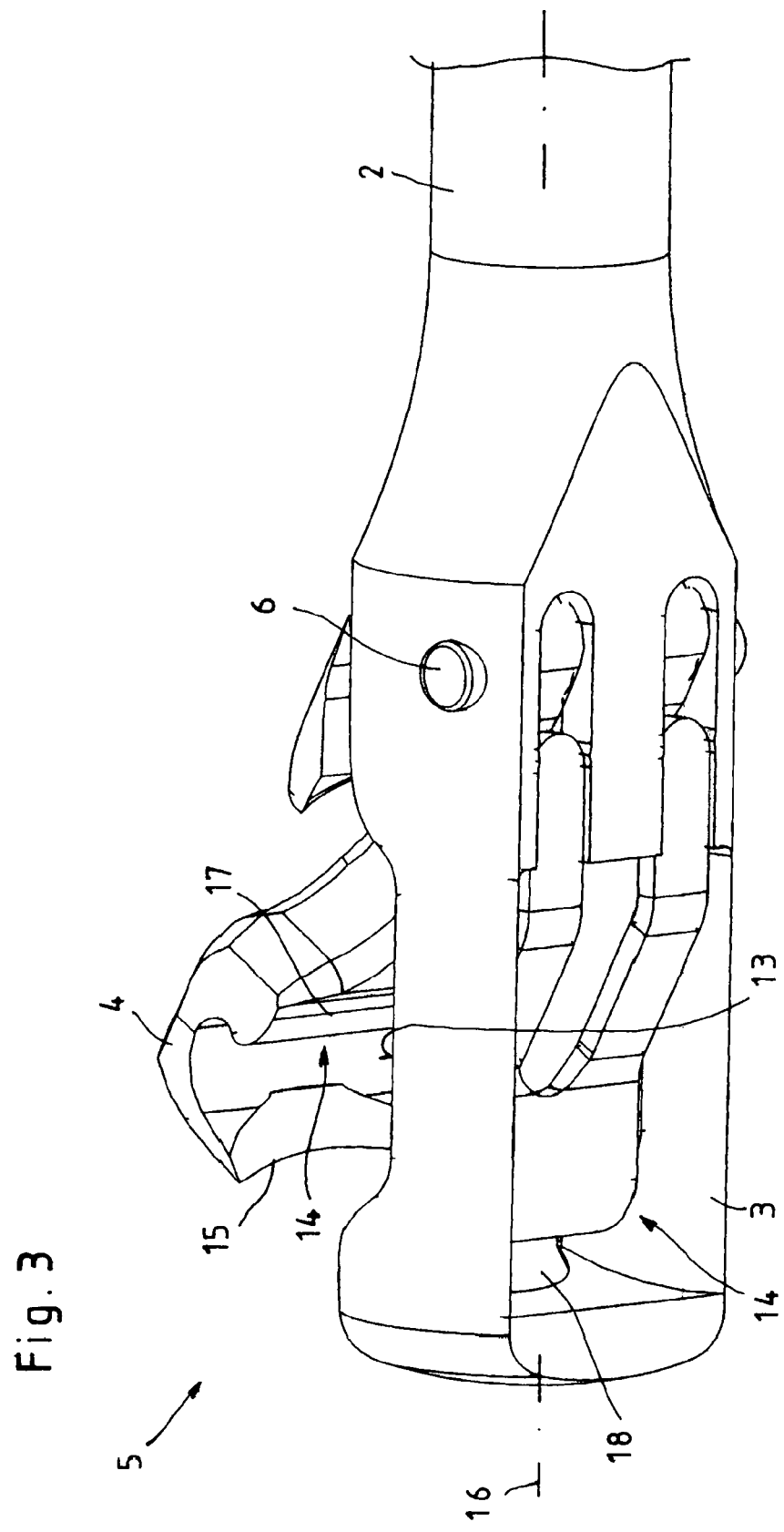
FIG. 3 shows a view from below of the depiction in FIG. 2.

The pivotable jaw member 4 of the tool 5 and the pivotable gripping member 9 of the handle 7 operatively interact with one another by way of an actuation element 11 mounted in the shaft 2, in such a way that the pivotable jaw member 4 can be converted by actuation of the pivotable gripping member 9 between a closed position contiguous with the rigid jaw member 3 (FIGS. 4, 6 and 7) and an opened position pivoted with respect to the rigid jaw member 3 (FIGS. 1 through 3). By means of the rigid jaw member 3, it is possible to achieve an especially advantageous guiding and thus positioning of the tendon during cutting, resulting in a substantially better cutting outcome in subcutaneous use of the cutting instrument 1.

Alternatively to the illustrated embodiment of the cutting instrument 1 with a rigid jaw member 3 and a pivotable jaw member 4, it is also possible of course to configure both jaw members as pivotable. A variant with two pivotable jaw members proves especially appropriate precisely for free-floating, freely dissectible tendons.

Moreover, the illustrated pivoting of the jaw member 4 with respect to the other jaw member 3 is only one embodiment for reciprocal displacement of the jaw members 3 and 4 with respect to one another. In addition to pivoting around the pivot axis 6, it is also possible to slide the jaw members 3 and 4 axially with respect to one another.

Figure 4:
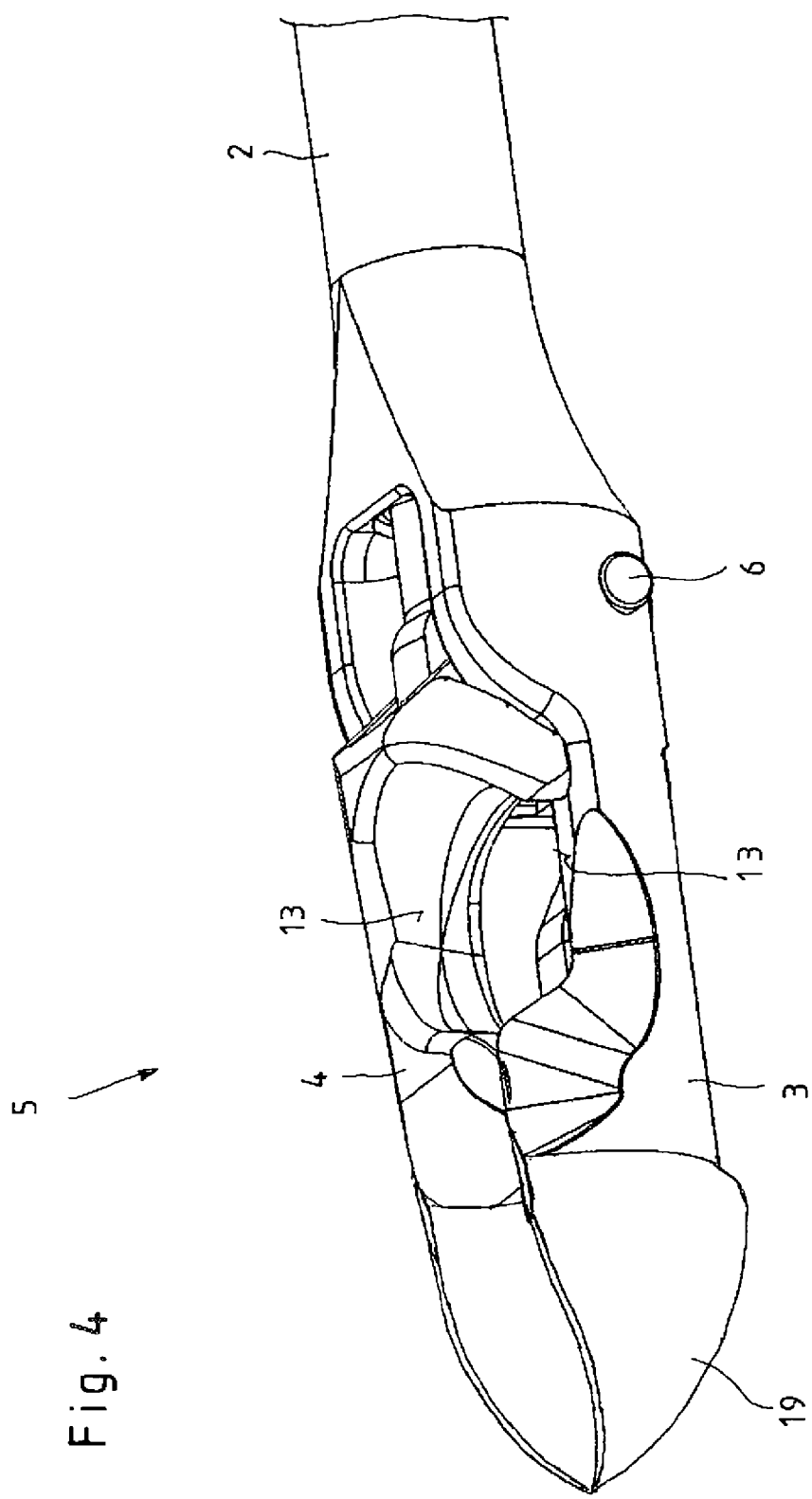
FIG. 4 shows a view according to FIG. 2 but depicting a second inventive embodiment in closed position.

The structure of the distal-end tool 5, consisting of jaw members 3 and 4, can be seen in particular from the enlarged detail views in FIGS. 2 through 4 as well as FIGS. 6 and 7.

In the illustrated embodiments, guides 13 configured as recesses 13 are made in both jaw members 3 and 4 to guide and receive the muscle/tendon tissue 12 (FIG. 1) that is to be cut.

The peculiarity of the illustrated tool 5 is that said tool 5 is configured to simultaneously sever and hold one end of the severed muscle/tendon tissue 12. In this way it is possible to prevent the severed muscle/tendon tissue 12, after severing, from withdrawing back to the base if the muscle/tendon tissue 12 has not previously been secured, for example by arthroscopic suturing.

To configure this dual clamping-cutting function, on the one hand mutually corresponding clamping surfaces 14 are positioned on the rigid jaw member 3 and on the pivotable jaw member 4 and on the other hand a cutting edge 15 is configured, at least on the pivotable jaw member 4. In these embodiments the clamping surfaces 14 are configured as toothed connections 17 aligned diagonally to the instrument longitudinal axis 16. The interlocking of the toothed connections 17 ensures a secure, slip-proof grip for the muscle/tendon tissue 12 mounted between the clamping surfaces 14.

The cutting edge 15 is oriented downward toward the rigid jaw member 3 and disposed on the distal end of the pivotable jaw member 4 in such a way that the muscle/tendon tissue 12 mounted in the guides 13 of the jaw members 3 and 4 is severed as soon as the pivotable jaw member 4 of the tool 5 is completely closed. Moreover, after severing the muscle/tendon tissue 12 by means of the cutting edge 15, to ensure that the end of the severed muscle/tendon tissue 12 that is situated in the proximal part of the tool 5 is held securely by the mutually corresponding clamping surfaces 14 of the jaw members 3 and 4, in the area of the cutting edge 15 situated on the pivotable jaw member 4 a recess 18 configured as an opening 18 is made in the rigid jaw member 3 to receive the cutting edge 15.

Said recess 18 in the rigid jaw member 3 of the tool 5 ensures that the pivotable jaw member 4 of the tool 5 can be closed completely and is not stopped by the cutting edge 15 running up against the rigid jaw member 3. Alternatively to the configuration of the recess 18 as a flow-through opening 18, it is also possible of course to configure the recess 18 as a non-open indentation in the rigid jaw member 3.

The placement of the clamping surfaces 14 on the jaw members 3 and 4 can be seen from a comparison of the drawings in FIGS. 2 and 3, according to which the clamping surface 14 is mounted on the pivotable jaw member 4 proximally behind the cutting edge 15 and the clamping surface 14 is mounted on the rigid jaw member 3 proximally behind the recess 18.

FIG. 4 shows a second, alternative embodiment for configuring the tool 5.

In this alternative embodiment, the distal end 19 of the rigid jaw member 3, which extends beyond the pivotable jaw member 4 in the axial direction, is additionally of rounded configuration in order to facilitate penetration of the medical cutting instrument 1 through soft parts by means of the dilator-shaped configuration of the distal instrument tip.

Figure 5:
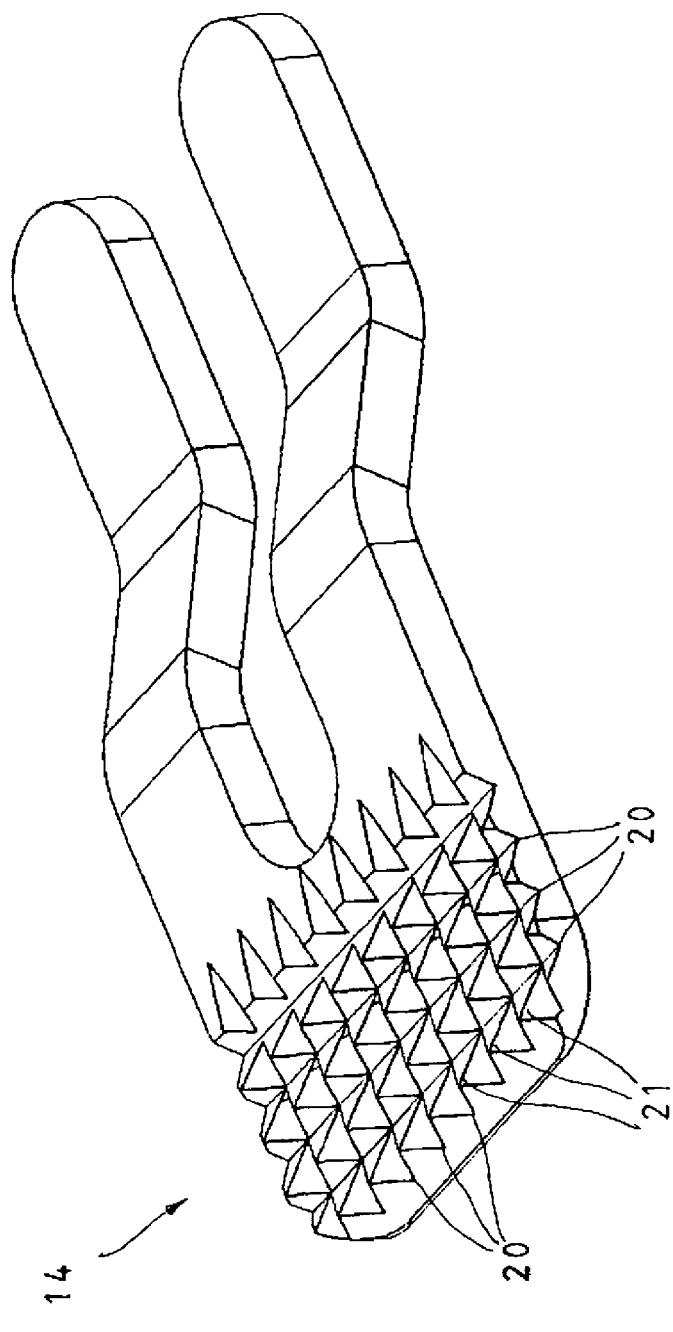
FIG. 5 shows a perspective view of a clamping surface according to a third inventive embodiment.

FIG. 5 shows an alternative embodiment for configuring the clamping surfaces 14. In this embodiment the clamping surfaces 14 are configured as individual teeth 21 separated from one another by diagonal and lengthwise indentations 20. The configuration as individual teeth 21 ensures a secure grip and a good lateral slip-proof security for the severed muscle or tendon tissue 12.

The toothed connection 17 or individual teeth 21 configured on the clamping surfaces 14 and oriented diagonally are advantageously configured as inclined toward the distal side to ensure better wedging and securing of the severed muscle or tendon tissue 12. Because of the inclination toward the distal end, the muscle or tendon tissue 12, which tries to withdraw back toward the proximal end, is pressed more firmly against the toothed connection 17 or the individual teeth 21.

FIGS. 6 and 7, finally, show an alternative embodiment for configuring the clamping surfaces 14. In this embodiment the clamping surface 14 on the rigid jaw member 3 is configured as a solitary individual tooth 24, while the clamping surface 14 on the pivotable jaw member 4 is configured as a row of teeth 25 running along the arc-shaped recess 13.

The solitary individual tooth 24, preferably mounted essentially centered on the rigid jaw member 3, presses the muscle/tendon tissue 12 that is to be held against the row of teeth 25 of the pivotable jaw member 4, with the jaw members 3 and 4 in closed position, and thus ensures the secure grip of the severed muscle/tendon tissue 12.

As can further be seen from FIG. 1, to adjust and shift the cutting depth a lever mechanism 22 is provided on the handle 7 that configures a variable stop for closing the two jaw members 3 and 4 with respect to one another and thus effects the shift in cutting depth.

Also foreseen on the handle 7 is a scale 23 that can be read from the outside, so that the muscle/tendon tissue can be severed by choice at a determined depth by actuating the lever mechanisms 22.

As a result of the configuration of the previously described medical cutting tool 1 as a combined cutting and holding tool, it is possible for the first time to grasp firmly by clamping one end of the muscle or tendon tissue 12 that has been severed in the first working step with the same cutting instrument 1, and thus to prevent it from withdrawing and keep it available for further surgical use.

What is claimed is:

1. A medical cutting instrument for cutting muscles and tendons, comprising:
    a shaft,
    a tool mounted on a distal end of the shaft, the tool comprising two jaw members, such that at least one moveable first jaw member is configured as a jaw member that can be moved with respect to one other second jaw member and on whose proximal end a handle is mounted, such that the at least one movable first jaw member and the handle operatively interact with one another by way of an actuation element mounted in the shaft, in such a way that the at least one movable first jaw member can be shifted by actuating the handle between a closed position and an opened position of the tool and such that the tool is configured for simultaneously severing and holding one end of the severed muscle/tendon tissue,
    at least on the at least one movable first jaw member a cutting edge is configured, wherein the cutting edge is mounted on a distal end of the at least one first movable jaw member oriented toward the other second jaw member and wherein mutually corresponding clamping surfaces are mounted on both first and second jaw members, and
    a guide for controlled insertion of the muscle/tendon tissue that is to be severed is configured at least in the other second jaw member, wherein the guide is configured as an arc-shaped recess formed on an outer lateral edge of the second jaw member and open toward the at least one movable first jaw member and being aligned transverse with respect to the cutting edge of the at least one movable first jaw member, and wherein the guide ensures that the muscle/tendon tissue that is to be severed is aligned correctly with the cutting edge and with the clamping surfaces.

2. The medical cutting instrument according to claim 1, wherein the guide is configured in both jaw members.

3. The medical cutting instrument according to claim 1, wherein the clamping surfaces are configured as toothed connections aligned diagonally to the instrument longitudinal axis.

4. The medical cutting instrument according to claim 3, wherein the diagonally aligned toothed connection and/or individual teeth are at least partially inclined toward a distal end.

5. The medical cutting instrument according to claim 1, wherein the clamping surfaces are configured as individual teeth separated from one another by diagonal and lengthwise indentations.

6. The medical cutting instrument according to claim 1, wherein clamping surfaces are configured as a solitary individual tooth mounted on the other second jaw member and as a row of teeth running along a recess on the at least one movable first jaw member.

7. The medical cutting instrument according to claim 6, wherein the solitary individual tooth is a single tooth mounted on the center of the other second jaw member.

8. The medical cutting instrument according to claim 1, wherein the cutting edge is of a U-shaped configuration and is mounted on the at least one movable first jaw member oriented toward the other second jaw member in such a way that the cutting edge extends from the distal end of the at least one movable first jaw member to both lateral areas of the at least one movable first jaw member.

9. The medical cutting instrument according to claim 1, wherein in an area of the cutting edge mounted on the at least one movable first jaw member, a recess for insertion of the cutting edge is configured in the other second jaw member.

10. The medical cutting instrument according to claim 9, wherein the recess is configured as an indentation or a pass-through opening.

11. The medical cutting instrument according to claim 9, wherein a clamping surface on the at least one movable first jaw member is mounted proximally behind the cutting edge and/or the clamping surface on the other second jaw member is mounted proximally behind the recess.

12. The medical cutting instrument according to claim 1, wherein a distal end of the other second jaw member, which extends beyond the at least one movable first jaw member in the axial direction, is of rounded configuration.

13. The medical cutting instrument according to claim 1, wherein in an area of the handle a lever mechanism is mounted that constitutes a variable stop for closing the jaw members with respect to one another and thus causes a shift in the cutting depth.

14. The medical cutting instrument according to claim 13, wherein a scale is mounted on the handle to determine the cutting depth.

15. A medical cutting instrument, comprising:
   a shaft;
   a tool mounted on a distal end of the shaft, the tool comprising a first jaw member and a second jaw member, the first jaw member being moveable with respect to the second jaw member, the first jaw member comprising a first clamping surface and the second jaw member comprising a second clamping surface that corresponds to the first clamping surface, the first jaw member comprising a cutting edge on a distal end thereof, the cutting edge being oriented toward the second jaw member, the second jaw member comprising a guide, the guide being an arc-shaped recess formed on an outer lateral edge of the second jaw member and configured to control insertion of a muscle and/or tendon tissue that is to be severed and to ensure that the muscle and/or tendon tissue is aligned correctly with the cutting edge and with the first and second clamping surfaces; and
   a handle mounted to a proximal end of the shaft, the handle being configured to operatively interact with the first jaw member by way of an actuating element mounted in the shaft, such that the first jaw member can be shifted by actuating the handle between a closed position and an opened position, and such that the tool is configured for simultaneously severing and holding one end of the muscle and/or tendon tissue after severing.

* * * * *